United States Patent [19]

Holtkamp, Sr.

[11] Patent Number: Plant 6,438

[45] Date of Patent: Dec. 6, 1988

[54] AFRICAN VIOLET PLANT NAMED SAGITARIUS

[76] Inventor: Reinhold Holtkamp, Sr., Werther Strasse 112, D4294 Isselburg, Fed. Rep. of Germany

[21] Appl. No.: 21,738

[22] Filed: Mar. 4, 1987

[51] Int. Cl.[4] ..... A01H 5/00
[52] U.S. Cl. ..... Plt./69
[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of African violet named Sagitarius characterized by its single deep blue flower with white wavy edges; strong, upright flower stems that curve toward the center to form a bouquet above the leaves; girl-type leaves; profuse flowering, vigorous growth habit, flowering 9–10 weeks after potting, and its long-lasting and non-dropping flowers.

1 Drawing Sheet

The present invention comprises a new and distinct cultivar of African violet plant, botanically known as *Saintpaulia ionantha,* and hereinafter referred to by the cultivar name Sagitarius.

The new cultivar was referred to during the breeding and selection process by the designation H26/4, and is a product of a planned breeding program. The new cultivar was originated from a cross made by me in the controlled breeding program in Isselburg, Federal Republic of Germany. The female, or seed parent, was a cultivar designated 13 Blue Girl. The male, or pollen parent, was a cultivar designated E 194 Blue White Edge.

Sagitarius was discovered and selected by me as a flowering plant within the progeny of the stated cross in a controlled environment in Isselburg, Federal Republic of Germany. Asexual reproduction of the new cultivar by leaf cuttings, as performed by me in 1982 at Haffen, Federal Republic of Germany, has demonstrated that the combination of characteristics as herein disclosed for the new cultivar are firmly fixed and retained through successive generations of asexual reproduction.

Sagitarius has not been observed under all possible environmental conditions. The phenotype may vary significantly with variations in environment such as temperature, light intensity and day length. The following observations, measurements and values describe the new cultivar as grown in Haffen, Federal Republic of Germany, and Nashville, Tenn., under greenhouse conditions which closely approximate those generally used in commercial practice.

The following traits have been repeatedly observed and are determined to be basic characteristics of Sagitarius, which in combination, distinguish this African violet as a new and distinct cultivar:

(1) Strong, upright flower stems curving toward the center.

2) Long-lasting, non-dropping, single deep-blue flowers with white wavy edge.

(3) Profuse flowering.

(4) Each plant carries 7–8 and more upright flower stems, each of which carries 7–9 flowers.

(5) Vigorous grower.

(6) Plant saleable 9–10 weeks after potting.

(7) Seed capsules push slightly through.

(8) Very attractive girl-type leaves, strongly serrated, with indentations and a white to light green center.

(9) After maturity the flowers dry off, and remain on the peduncle without becoming infected by botrytis.

Sagitarius is similar to the cultivar Houston in the characteristics of girl-type leaves and primary deep-blue flower color. The principal distinguishing feature of Sagitarius when compared with Houston is the white edge around the flower petals.

The accompanying color photographic drawing shows a typical specimen plant of the new cultivar. The colors appearing in the photograph are as true as possible with color illustrations of this type.

In the following description, color references are made to the Royal Horticultural Society Colour Chart (RHS), except where general colors of ordinary significance are referred to. Color values were taken under natural sunlight conditions at approximately 2:00 in Nashville, Tenn.

Botanical classification: *Saintpaulia ionantha,* Ramat., cv. Sagitarius.

Parentage:

*Male parent.*—E 194 Blue White Edge.

*Female parent.*—13 Blue Girl.

Propagation: The new cultivar holds its distinguishing characteristics through successive propagations by leaf cuttings.

Plant: From 9 cm to 11 cm tall when grown in pots, and approximately 18–20 cm in diameter when fully grown.

*Leaves.*—General form: Round girl-type. Diameter: 60–75 mm. Texture: Velvety, shiny. Aspect: Serrated, indented, hairy, bright, light green center radiating along the veins. Veins: Upperside: visible, light green towards the center; underside: very well pronounced, very light green, shiny. Purplish red on the very young leaves. Color (upper side): Yellow green 147A. Color (under side): Yellow green 148D. Petiole: Strong, upright, light green, sometimes with purplish touch, expecially on young leaves, hairy.

Flowers.—Buds: Bell-shaped, 8–9 mm just before opening, purple blue petals with greenish white edge already very visible. Sepals: Five (5). Color: Purplish green. Calyx: Shape: Funnelshaped. Aspect: Spear-shaped, hairy. Peduncle: Character: Strong, upright, hairy. Color: Purplish brown. Individual flowers: Size: 40–45 mm. Shape: Single violet shaped; 3 large and 2 small, almost round, petals. Color (upper side): 86A–87A with white edges. Color (under side): 87B. Borne: Each flower stem carries 7–9 and more flowers on strong, upright peduncles, are free-standing above the leaves, and curved toward the center of the plant. Flowering habit: Flowers 9–10 weeks after potting, with a compact, flower head forming above the leaves.

*Reproductive organs.*—Stamens: 2. Anthers: 2 composed of 4 cells. Filaments: light green blue traces, 4 mm. Pollen color: Yellow 7A. Styles: 7 mm, purplish blue, with a light green, hairy base of ovary.

*Roots.*—Normally developed, white when young, turning slightly brownish when older.

Disease resistance: Good.

General observations: Sagitarius has a very attractive appearance due to its deep blue flowers with a wavy white edge contrasting with the bright yellow anthers. A tight bouquet of flowers on strong peduncles stands free above a bright green, strongly serrated girl-type leaves that have bright light green centers. Occasionally, 1 or 2 additional small petals develop over the 2 smaller petals. The flowers are long-lasting and non-dropping.

I claim:

1. A new and distinct cultivar of African violet named Sagitarius, as described and illustrated, and particularly characterized by its single deep blue flower with white wavy edges; strong, upright flower stems that curve toward the center to form a bouquet above the leaves; girl-type leaves; profuse flowering, vigorous growth habit, flowering 9–10 weeks after potting, and its long-lasting and non-dropping flowers.

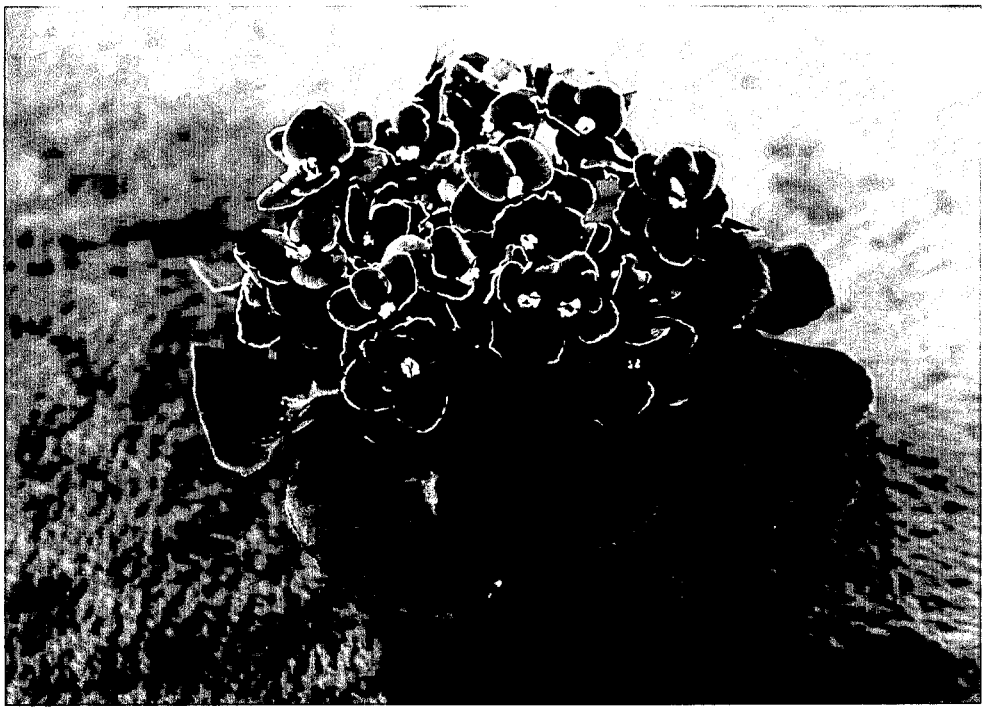

* * * * *